United States Patent [19]

Schramm

[11] Patent Number: 4,817,632
[45] Date of Patent: Apr. 4, 1989

[54] ORAL FLUID COLLECTION ARTICLE

[75] Inventor: Willfried Schramm, Ann Arbor, Mich.

[73] Assignee: BioQuant, Inc., Ann Arbor, Mich.

[21] Appl. No.: 65,559

[22] Filed: Jun. 23, 1987

[51] Int. Cl.[4] .............................................. A61B 5/00
[52] U.S. Cl. .................................................... 128/769
[58] Field of Search ............... 128/636, 760, 762, 767, 128/769; 604/93, 285, 286, 317, 358, 365, 367; 210/321.75

[56] References Cited

U.S. PATENT DOCUMENTS

| Re. 29,061 | 12/1976 | Bucalo | 604/55 |
|---|---|---|---|
| 3,688,763 | 9/1972 | Cramarty | 128/769 |
| 3,797,496 | 3/1974 | Loiacono | 604/286 |
| 3,885,312 | 5/1975 | Nordin . | |
| 3,890,712 | 6/1975 | Lopez . | |
| 3,913,231 | 10/1975 | Orsing . | |
| 3,947,328 | 3/1976 | Friedenberg et al. . | |
| 3,968,011 | 7/1976 | Manautou et al. . | |
| 4,016,794 | 4/1977 | Brown . | |
| 4,017,975 | 4/1977 | Johnson . | |
| 4,019,255 | 4/1977 | Cohen et al. . | |
| 4,066,405 | 1/1978 | Henkin . | |
| 4,071,026 | 1/1978 | Bevins . | |
| 4,074,435 | 2/1978 | Orsing . | |
| 4,083,115 | 4/1978 | McKelvey . | |
| 4,088,788 | 5/1978 | Ream et al. . | |
| 4,114,605 | 9/1978 | McGhee et al. | 128/760 |
| 4,172,446 | 10/1979 | Bucalo | 128/769 |
| 4,197,288 | 4/1980 | Snyder . | |
| 4,233,288 | 11/1980 | Cornell . | |
| 4,260,378 | 4/1981 | O'Neil . | |
| 4,358,288 | 11/1982 | Goldman . | |
| 4,385,125 | 5/1983 | Preti et al. . | |
| 4,418,702 | 12/1983 | Brown et al. . | |
| 4,431,742 | 2/1984 | Rosenblatt . | |
| 4,438,100 | 3/1984 | Balslev et al. . | |
| 4,519,400 | 5/1985 | Brenman et al. . | |
| 4,580,577 | 4/1986 | O'Brien et al. | 128/760 |
| 4,595,011 | 6/1986 | Phillips | 128/636 |
| 4,612,008 | 9/1986 | Wong et al. | 604/285 |
| 4,635,488 | 1/1987 | Kremer | 128/760 |

OTHER PUBLICATIONS

Baurmeister et al., Symposium 'Biocompatibilite des Membranes en Hemodialyse' Grenoble, France; Nov. 1984.
Immunossays of Steroids in Saliva, Alpha Omega Publishing Ltd, Cardiff 1982.
Horning et al., Clin. Chem. 23:157–164, 1977.
K. S. Lashley, J. exp. Psychol. 1:461–493, 1916.
E. L. Truelove, D. Bixler, A. D. Merritt, J. dent. Res. 46:1400–1403, 19671.

Primary Examiner—Max Hindenburg
Attorney, Agent, or Firm—Reising, Ethington, Barnard, Perry & Milton

[57] ABSTRACT

The present invention is an oral fluid collection article for placement in the buccal cavity of an individual for the collection and fittering of a saliva fluid. The collection article has a semi-permeable membrane container enclosing an osmotic substance means.

13 Claims, 2 Drawing Sheets

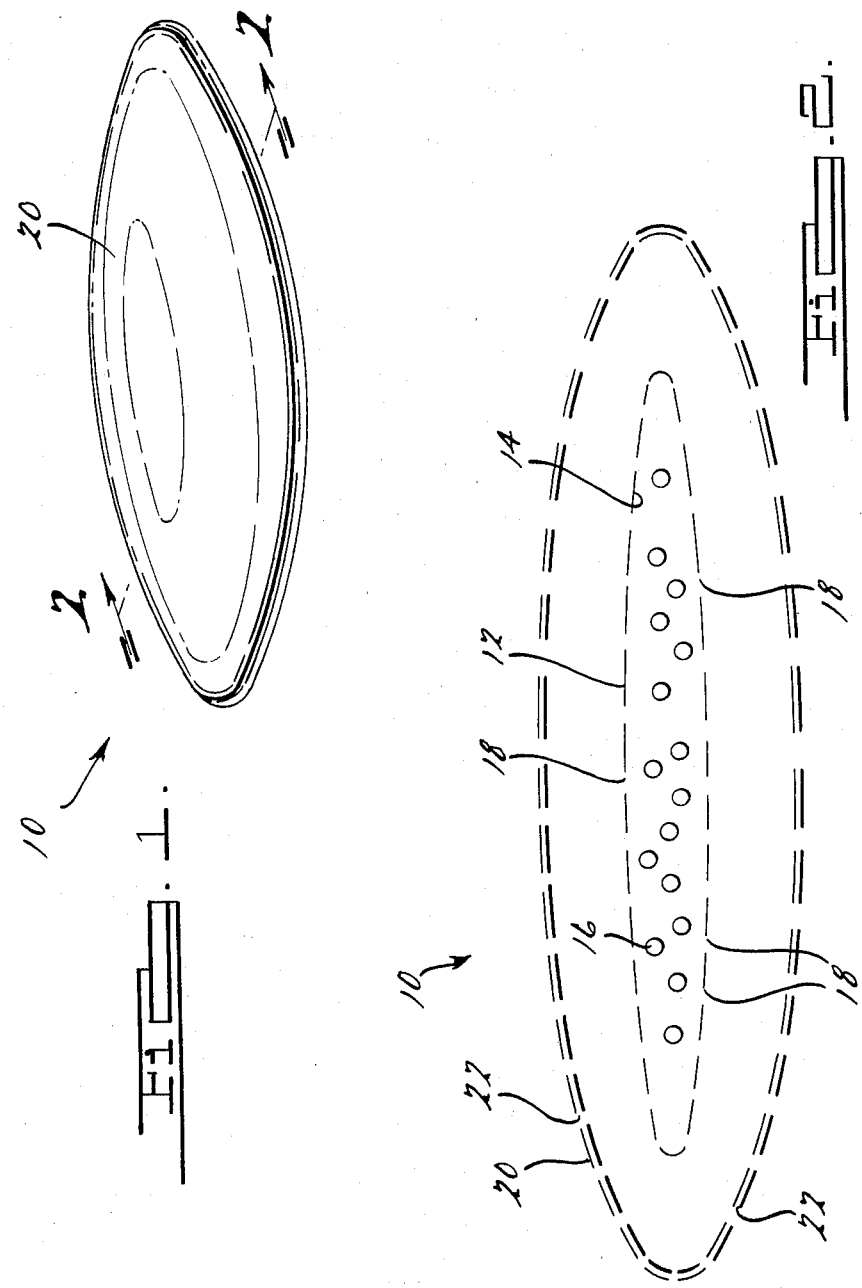

ORAL FLUID COLLECTION ARTICLE

BACKGROUND

The present invention relates to the sampling of oral fluids from an individual. More particularly the present invention relates to a saliva and oral fluid collection article to be used in the buccal cavity of a patient.

The sampling and testing of body fluids has long been used in the medical field to test and monitor the human body for various biochemical or physiological conditions or elements or just generally the state of health of a patient's body. Commonly, blood and urine samples are taken from patients for analysis to determine various levels of electrolytes, drops, hormones, metabolites, or other physiologically relevant biochemicals of the body. Recently, it has been found that a person's oral fluids or saliva may also be analyzed to provide valuable information regarding various biochemicals. It has been found that for a large number of molecules, direct correlation exists between the concentrations of particular substances in blood with that contained in oral fluids or saliva and also the concentrations of substances in urine correlate with those contained in saliva. Therefore, recently saliva has become a more desirable medium for monitoring of hormones, drugs, metabolites, or other physiologically relevant biochemicals in clinical chemistry and related fields.

The use of saliva as a testing medium is desirable since the saliva of a patient is readily available without the intrusive methods required in sampling of blood, by the use of syringes or other methods for instance, and without the undesirable nature of urine sampling which may cause other problems, such as monitoring of a patient while taking of a sample. Therefore use of saliva as a medium in biochemical and physiological analyses is desirable since it can be obtained by non-invasive methods.

While it has been found that saliva can be advantageously used in the analysis of the body's biochemistry there remain problems in the collection of saliva and in the handling of saliva by laboratory technicians. For instance, saliva contains mucopolysaccharides which contribute to the highly viscous, stringy or sticky consistency which creates problems in pipetting and measuring of the saliva. There are also sampling and handling problems due to the presence of particulate matter in the form of oral squames which preferably must be removed before analysis. Additionally, food or other particulate matter in the mouth presents further undesirable handling problems in that the particles must be removed from the sample before analysis. In addition, the intake of food substances can drastically affect the consistency and the appearance of saliva for extended periods of time further increasing the variable consistency and requiring difficult processing prior to analysis. Moreover, conditions of food substances can interfere with the analysis of saliva for both qualitative and quantitative measurements.

Variations in the consistency and contents of saliva also creates problems in its handling such that a centrifugal apparatus or other filtering or separation device must be used to separate and purify the sample from the undesirable particulate matter contained in the saliva prior to analysis. Additionally, the pipetting and measuring of saliva is difficult due to the stringy or viscous consistency. For these reasons, it is difficult for technicians to handle samples of saliva.

The sampling of saliva from patients may create further problems in that it is hard to obtain the sample inconspicuously from a patient. For instance, in curtain conditions if a patient knows that saliva is going to be collected this might have the adverse psychological effect of causing the patient's mouth to become dry thus creating problems in taking of a saliva sample. Additionally, some patients may even be hesitant to agree to sampling of saliva in their mouth or to expectorate for various reasons.

Saliva might contain large molecules or other components which might intefere with further analysis. For example, many hormones and drugs in saliva reflect the "free" component in blood, i.e. the fraction which is not bound to proteins. This fraction might constitute only a small percentage of the total amount ("bound" and "free") in blood. However, through small lacerations of the gum or the cheeks, blood, containing substances bound to protein(s), might enter the oral cavity and substantially increase the total concentration of substance to be analyzed. Thus, some "bound" substance might constitute a substantial amount of the total substance measured and be erroneous interpreted as "free". Thus, it is desirable to exclude larger molecules such as binding proteins. In another example, some enzyme proteins metabolize saliva components to metabolites. Thus, for accurate measurement of substances subject to enzymatic degradation, rapid and complete separation of enzymes from remaining fluid is required.

SUMMARY OF THE INVENTION

Therefore, according to the present invention, there is provided on oral fluid collection article which is adapted for placement in the buccal cavity of a patient for the collection and filtering of an oral fluid sample. The oral fluid collection article of the present invention comprises a semi-permeable membrane which defines an enclosed chamber. The semi-permeable membrane has pores which are of a size to allow desired oral fluid molecules to pass through but which will act as a filter for retaining larger undesirable particles or molecules from the oral fluid sample. An osmotic substance means is provided which is disposed in the enclosed chamber of the semi-permeable membrane. The osmotic substance means is for dissolving in the oral fluid which passes through the semi-permeable membrane and thereby creates an osmotic pressure for drawing the oral fluid from the buccal cavity of the patient into the chamber of the semi-permeable membrane. Thereby, the semi-permeable membrane retains in the enclosed chamber at least a portion of the oral fluid.

It is an object of the present invention to provide an oral fluid collection article which is less intrusive in obtaining an oral fluid sample from a patient.

It is a further object of the present invention to provide an oral fluid collection device which uses osmotic pressure by which to draw an oral fluid sample into a chamber in the fluid collection article.

It is still further an object of the present invention to provide an oral fluid collection article which not only samples an oral fluid but also filters particular matter from the fluid thereby requiring little further preparation by laboratory technicians or other people prior to analysis of the fluid sample.

It is still further an object of the present invention to provide an oral fluid collection article which can exclude large molecules including enzymes and binding proteins from entering the enclosed chamber containing the fluid sample to be analyzed.

THE DESCRIPTION OF THE DRAWINGS

Other advantages of the present invention will be readily appreciated as the same becomes better understood by reference to the following description when considered in connection with the accompanying drawings wherein:

FIG. 1 is a perspective view of the fluid collection article of the present invention;

FIG. 2 is a cross-sectional view along line 2—2 of FIG. 1 showing the oral fluid collection device of the present invention;

DESCRIPTION OF THE PREFERRED EMBODIMENT

Figure 3:
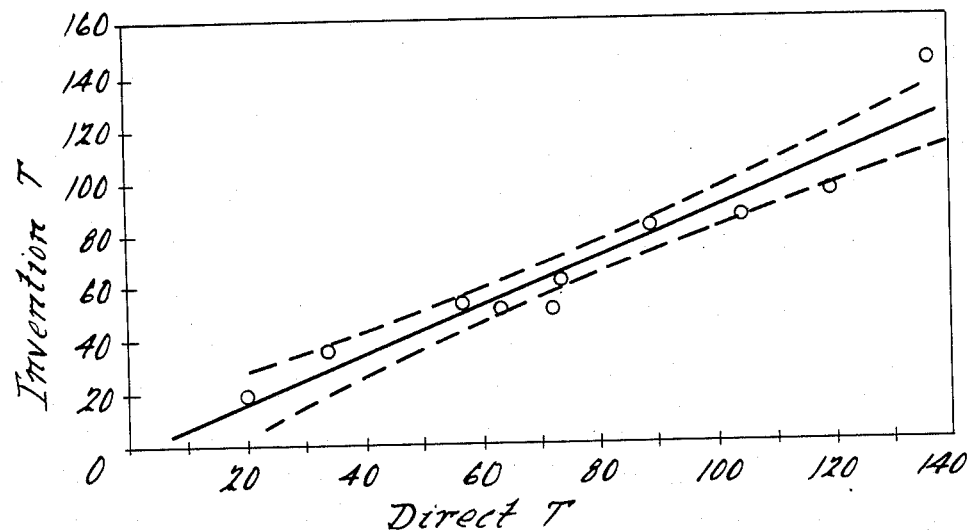
FIG. 3 is a chart showing the relation of testosterone analyzed in a saliva sample directly sampled and that collected with the oral fluid collection article of the present invention.

Referring to FIG. 1 there is provided an oral fluid collection article generally shown at 10. Oral fluid collection article 10 is preferably an ovoid small disc or pillow shaped article which is adapted to fit conveniently in the mouth of a patient. As shown more particularly in FIG. 2, the oral fluid collection article 10 includes a semi-permeable membrane 12 which defines an enclosed chamber 14. As osmotic substance means 16 is provided which is totally enclosed by semi-permeable membrane 12.

The fluid collection article 10 of the present invention is adapted for placement entirely in the buccal cavity of an individual and allows for collection and filtering of an oral fluid/saliva sample. The semi-permeable membrane 12 is made of a substance which has a plurality of pores which are of a suitable size to allow salivary fluid to pass therethrough but which pores 18 also act as a filter for filtering out unwanted particulate matter or larger molecules such as binding proteins from the sample.

Osmotic substance means 16 is included inside the chamber 14 and is soluble in saliva thereby providing an osmotic pressure inside chamber 14 for drawing saliva from the buccal cavity of the patient into the chamber 14. After which time the semi-permeable membrane 12 will retain at least a portion of the fluid in chamber 14 for later removal by a technician for analysis.

The osmotic substance means 16 in a preferred embodiment includes a crystalline or amorphous material which is soluble in saliva and will allow interference-free analysis of the saliva sample for whatever particular analysis is being undertaken. Alternatively, the osmotic substance means could comprise a high molarity solution of a crystalline or amorphous material which is dissolved in water or some other non-interferring solute. Of course, since the article of the present invention is for use in the buccal cavity of a patient, these materials should be nontoxic in nature and if possible should be palatable and may even by of a material which produces a pleasurable taste which may further increase the patient's salivation process. The material used may be a carbohydrate of small molecular weight which is biologically inert and which will be readily soluble in water and more particularly soluble in saliva. In a preferred embodiment of the present invention the crystalline material is glucose, fructose, or sucrose, however, other materials may be used which have the desirable characteristics as stated above. In another embodiment, the material might be a nontoxic polymer which creates an osmotic pressure by accommodating water molecules. The osmotic substance chosen must also be compatible with the analysis which is to be performed on the final sample, such that the substance chosen will not interfere with any testing being undertaken on the final saliva sample collected, since the sample will generally contain some of the osmotic substance 16.

Whatever the osmotic substance 16 used, the substance must be soluble in saliva or accommodate water molecules, whereby saliva passing through the semi-permeable membrane 12 will dissolve the material or be accommodated by the material and produce a high molarity solution with the saliva and the osmotic substance 16 inside semi-permeable membrane 12. This will then produce an osmotic pressure system whereby the saliva from the outer portion of the semi-permeable membrane, i.e. the buccal cavity, will be drawn into the chamber 14 through the membrane 12 due to the difference in osmotic pressure on the inner side of the membrane and the saliva outside of the membrane thereby setting up an osmotic pump for drawing a saliva sample into the chamber 14. In some embodiments of the invention the solution inside the chamber 14 will be exchanged to the mouth of the patient. However, this exchange is not necessary for operation of the present invention as long as saliva is "pumped" into the chamber 14.

The semi-permeable membrane 12 may be of any of a variety of semi-permeable materials. Preferably the material used is a cellulose film material. The pores 18 may be of any size which are of use for selectively filtering out undesirable materials while allowing desirable saliva molecules to pass through into the chamber 14 and allowing free exchange of the inner solution containing the osmotic substance from inside the chamber 14 into the patient's mouth. Thus the size of pores 18 may be controlled and selected according to the pertinent application to exclude larger molecules. In a preferred embodiment of the invention the semi-permeable membrane 12 is a 40 millimeter length of tubing having a 14.3 millimeter radius which is sealed at both ends. The tubing used is a Cuprophan dialysis tubing material. Cuprophan is a trademark of Enka, A. G. of Wuppertal, West Germany. The tubing material is sealed at both ends by tying with string or other means, preferably the semi-permeable membrane is formed as an ovoid or pillow shaped integral unit. The inner chamber preferably contains approximately 1-2 grams of sucrose.

Figure 4:
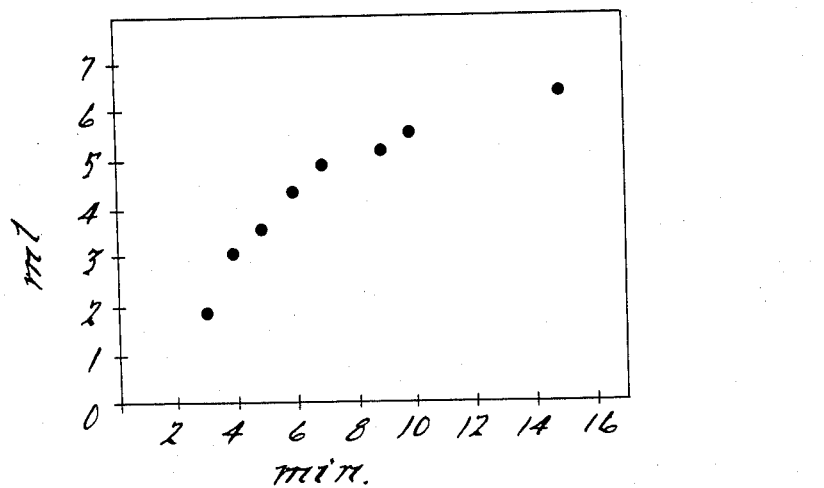
FIG. 4 is a chart showing the collection of oral fluid in the present invention over time.

Shown in FIG. 4 is the amount of saliva collected by the above described embodiment over periods of time. The quantity of sample collected is set forth on the absissa of the graph and the time required for sampling in minutes is shown on the ordinate. For this embodiment, a 4 milliliter sample of clear saliva is usually obtained in approximately five minutes as is shown by FIG. 4. Thus the present invention provides a sufficient sample in a reasonable period of time, which is relatively pure and ready for direct analysis.

The sample collected in the present invention is easily removed from the chamber 14 by use of a needle attached to a syringe or by other methods. Thus the sample can be transferred to suitable analytic equipment for desirable tests to be run on the sample.

If desirable, the semi-permeable membrane 12 may be enclosed by an outer protective membrane 20 which includes macroscopic pores and is disposed about and completely enclosing the semi-permeable membrane 12. Outer protective membrane 20 is made of any material which would be generally pliable, tasteless, and non-toxic. Preferably the silicon materials or other materials should have a substantial mechanical strength which could protect the inner membrane from damage due to biting by a patient and similar hazards which may be associated with the use of the present invention in a patient's mouth.

The outer membrane 20 may be made of many materials whereby saliva easily passes through the macroscopic pores 22. Additionally, the article of the present invention may be practiced without the use of the outer membrane 20 wherein the inner membrane 12 is made of a material of a sufficient mechanical strength which will stand up to any hazardous problems which would be encountered within the mouth of the patient.

The substance 16 may also include an amount of a citric acid or ascorbic acid as a gustatory stimulus. This amount may be approximately 1–2% of the weight of the glucose material used within the chamber 14. This will increase the salivary flow from an individual but will not increase the volume of the saliva within the chamber 14 which is totally dependent on the osmotic pressure created therein.

The present invention is preferably formed in a ovoid shape or pillow shape, as shown in FIG. 1, such that it will readily fit in the cheek of an individual. However, the shape may be varied according to the particular application to which it will be used. Thus, in the present invention an oral fluid collection device is provided which is easily sterilizable and can be formed to fit desirably in the cavities of the mouth, allowing patients to talk and carry on normally while fluid is being sampled from their mouths. In addition, use of the materials stated such as glucose, fructose, or sucrose would not interfere with assays for steroid hormones or drugs as two examples.

Additionally, in the present invention the saliva sample is filtered as it is collected wherein the undesirable material including oral squames and bound proteins are filtered out of the sample prior to entering the chamber 14.

FIG. 3 is a chart showing the correlation of levels of testosterone analyzed in a saliva sample directly sampled as shown on the ordinate and that collected with the oral fluid collection article of the present invention represented on the absissa showing a 90% confidence interval in the results obtained with the samples taken according to the present invention. Thus, as shown in FIG. 3 the results of testosterone measurements in fluid obtained from the subject invention as disclosed herein are highly accurate as compared to the results obtained by commonly used procedures at the present time.

The invention has been described in an illustrative manner and it is to be understood that the terminology which has been used is intended to be descriptive rather than limitative. Obviously, many modifications and variations of the present invention are possible in light of the above teachings. Therefore, it is to be understood that within the scope of the appended claims the invention may be practiced otherwise than as specifically as described.

What is claimed is:

1. An oral fluid collection article for placement entirely in the buccal cavity of an individual for collection and filtering of a saliva fluid sample comprising: a semi-permeable membrane container defining an enclosed chamber, said semi-permeable membrane container having pores which are of a size to allow desirable oral fluid molecules to pass through, said pores acting as a filter for filtering out of larger undesirable particulate or molecular matter from said saliva; and osmotic substance means being disposed in said enclosed chamber for creating an osmotic pressure system inside of said chamber and for drawing oral fluid from said buccal cavity through said container and into said chamber of said semi-permeable membrane container and retaining at least a portion of said fluid in said chamber.

2. The oral fluid collection article of claim 1 wherein said osmotic substance means comprises a crystalline material which is soluble in saliva and will allow interference free analysis of the saliva sample.

3. The oral fluid collection article of claim 1 wherein said osmotic substance means comprises an amorphous material which accommodates water and will allow interference free analysis of the saliva sample.

4. The oral fluid collection article of claim 1 wherein said osmotic substance means comprises a high-molarity solution of a crystalline material being dissolved in water.

5. The oral fluid collection article of claim 1 wherein said osmotic substance means comprise a high molarity solution of an amorphous material being dissolved in water.

6. The oral fluid collection article of claim 1 wherein said osmotic substance means is a carbohydrate having a low molecular weight.

7. The oral fluid collection article of claim 1 wherein said osmotic substance means is taken from the group consisting of glucose, fructose and sucrose.

8. The oral fluid collection article of claim 1 wherein said osmotic substance means consists of a nontoxic polymer soluble in water.

9. The oral fluid collection article of claim 1 wherein in said osmotic substance consists of a nontoxic material which accommodates water.

10. The oral fluid collection article of claim 1 wherein said pores are of a size which will filter out particles having a size of about 25,000 daltons or greater.

11. The oral fluid collection article of claim 1 wherein said pores are of a size which allows osmotic pressure to be created in said chamber.

12. The oral fluid collection article of claim 1 further comprising: an outer protective membrane for containing and protecting said semi-permeable membrane container, said outer protective membrane being disposed about and enclosing said semi-permeable membrane container, said outer protective membrane having macroscopic pores for allowing said oral fluid to pass therethrough.

13. The oral fluid collection article of claim 12 wherein said outer protective membrane container is made of a non-toxic material.

* * * * *